(12) United States Patent
Wariar et al.

(10) Patent No.: US 8,337,408 B2
(45) Date of Patent: Dec. 25, 2012

(54) REMOTE MONITORING OF PATIENT COGNITIVE FUNCTION USING IMPLANTED CRM DEVICES AND A PATIENT MANAGEMENT SYSTEM

(75) Inventors: Ramesh Wariar, Blaine, MN (US); Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1899 days.

(21) Appl. No.: 11/457,247

(22) Filed: Jul. 13, 2006

(65) Prior Publication Data

US 2008/0033303 A1 Feb. 7, 2008

(51) Int. Cl.
*A61B 5/02* (2006.01)
(52) U.S. Cl. ........ 600/483; 600/300; 600/481; 600/544; 434/236; 434/322
(58) Field of Classification Search .................. 434/236, 434/322–364; 600/300, 301, 481–528, 544, 600/545; 702/182
See application file for complete search history.

(56) References Cited

U.S. PATENT DOCUMENTS

| | | | |
|---|---|---|---|
| 6,067,466 A * | 5/2000 | Selker et al. ................. | 600/513 |
| 6,740,032 B2 | 5/2004 | Balkin et al. | |
| 6,743,167 B2 | 6/2004 | Balkin et al. | |
| 6,820,037 B2 * | 11/2004 | Simon ......................... | 702/182 |
| 6,832,609 B2 | 12/2004 | Wright et al. | |
| 6,856,913 B1 | 2/2005 | Silberstein | |
| 6,964,638 B2 | 11/2005 | Theodoracopulos et al. | |
| 6,980,851 B2 * | 12/2005 | Zhu et al. .................... | 600/513 |
| 7,347,818 B2 * | 3/2008 | Simon ......................... | 600/300 |
| 2005/0053904 A1 | 3/2005 | Shephard et al. | |
| 2007/0167687 A1 * | 7/2007 | Bertolero et al. ............ | 600/300 |

OTHER PUBLICATIONS

Predictors of congestive heart failure in the elderly: the Cardiovascular Health Study. Gottdiener JS, Arnold AM, Aurigemma GP, Polak JF, Tracy RP, Kitzman DW, Gardin JM, Rutledge JE, Boineau RC. J Am Coll Cardiol. May 2000;35(6):1628-37.*
Almeida, O. P., et al., "Clinical treatment reverses attentional deficits in congestive heart failure", *BMC Geriatr.*, 1:2, (2001), 1-7.
Bennett, S. J., et al., "A Conceptual Model of Cognitive Deficits in Chronic Heart Failure.", *Journal of Nursing Scholarship*, 37(3), (2005), 222-228.
Bennett, S. J., et al., "Characterization of the Precipitants of Hospitalization for Heart Failure Decompensation.", *American Journal of Critical Care.*, 7(3), (May 1998), 168-174.
Bennett, S. J., et al., "Cognitive Deficits in Patients With Heart Failure: A Review of the Literature", *J Cardiovasc Nurs.*, 18(3) Jul.-Aug. 2003, 219-242.
Putzke, J. D., et al., "Neuropsychological functioning among heart transplant candidates: a case control study.", *J Clin Exp Neuropsychol.*, 22(1), (Feb. 2000),95-103.

(Continued)

*Primary Examiner* — Navin Natnithithadha
*Assistant Examiner* — Karen Toth
(74) *Attorney, Agent, or Firm* — Schwegman Lundberg & Woessner, P.A.

(57) ABSTRACT

This document discusses, among other things, a system and method for remote monitoring of patient cognitive function using implanted cardiac rhythm management (CRM) devices and a patient management system. The method comprising: presenting a cognitive test to a patient via a user interface; receiving a result of the cognitive test using the user interface; and using the result of the cognitive test in determining a heart failure condition status.

20 Claims, 4 Drawing Sheets

OTHER PUBLICATIONS

Tsuyuki, R. T., et al., "Acute Precipitants of Congestive Heart Failure Exacerbations.", *Arch Intern Med.*, 161(19), (Oct. 22, 2001), 2337-2342.

Zuccalà, G., et al., "The Effects of Cognitive Impairment on Mortality Among Hospitalized Patients with Heart Failure.", *Am J Med.*, 115(2), (Aug. 1, 2003), 97-103.

* cited by examiner

REMOTE MONITORING OF PATIENT COGNITIVE FUNCTION USING IMPLANTED CRM DEVICES AND A PATIENT MANAGEMENT SYSTEM

TECHNICAL FIELD

This patent document pertains generally to implantable medical devices, and more particularly, but not by way of limitation, to integrated health care home communication and monitoring.

BACKGROUND

Implantable medical devices (IMDs), including cardiac rhythm management devices such as pacemakers and implantable cardioverter/defibrillators, typically have the capability to communicate data with an external device, such as an external programmer, via a radio-frequency (RF) telemetry link. While an external programmer is typically provided to program and modify the operating parameters of an IMD, modern IMDs also include the capability for bidirectional communication so that information, such as physiological data, can be transmitted to the programmer. In turn, home health care monitoring systems can communicate with the programmer and collect the patient data. In addition, some monitoring systems can also collect other objective or subjective data using additional external sensors, such as a blood pressure cuff, a weight scale, or a specialized device that prompts the patient with questions regarding their health state. Home health care monitoring systems can communicate with a centralized system, either directly or through a networked system. Centralized systems provide an efficient mode for physicians and other medical practitioners to view patient data and communicate with their patients and with the medical community at large.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

BRIEF DESCRIPTION OF THE DRAWINGS

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls. Some patients with congestive heart failure (HF) exhibit a co-morbidity of decreased cognitive function. While certain patients may exhibit HF and cognitive impairment atypically, there may be a relationship of such co-morbidities. By monitoring a patient's cognitive function, a physician may be able to adaptively monitor and treat the patient's HF condition and reduce hospitalizations, improve patient outcomes, and increase the patient's quality of life. Using centralized information gathering systems, such as the one described above, a physician can monitor subjective and objective indications to quickly address patient decompensation.

In general, cognitive ability includes higher level brain functions, such as those related to memory, attention, problem solving, learning, and psychomotor function. Several factors can contribute to cognitive dysfunction, including age, depression, medication, hypertension, and disease, such as congestive heart failure. By capturing data over time that reflects cognitive function, trends that indicate a decrease in cognitive ability may be indicative of an onset or worsening of a disease condition. Internal and external sensors can collect data to later be stored and analyzed, such as at a centralized or other information system. Clinicians and other medical professionals can then access the stored data and use it to help diagnose a patient's heart failure disease condition status.

Figure 1:
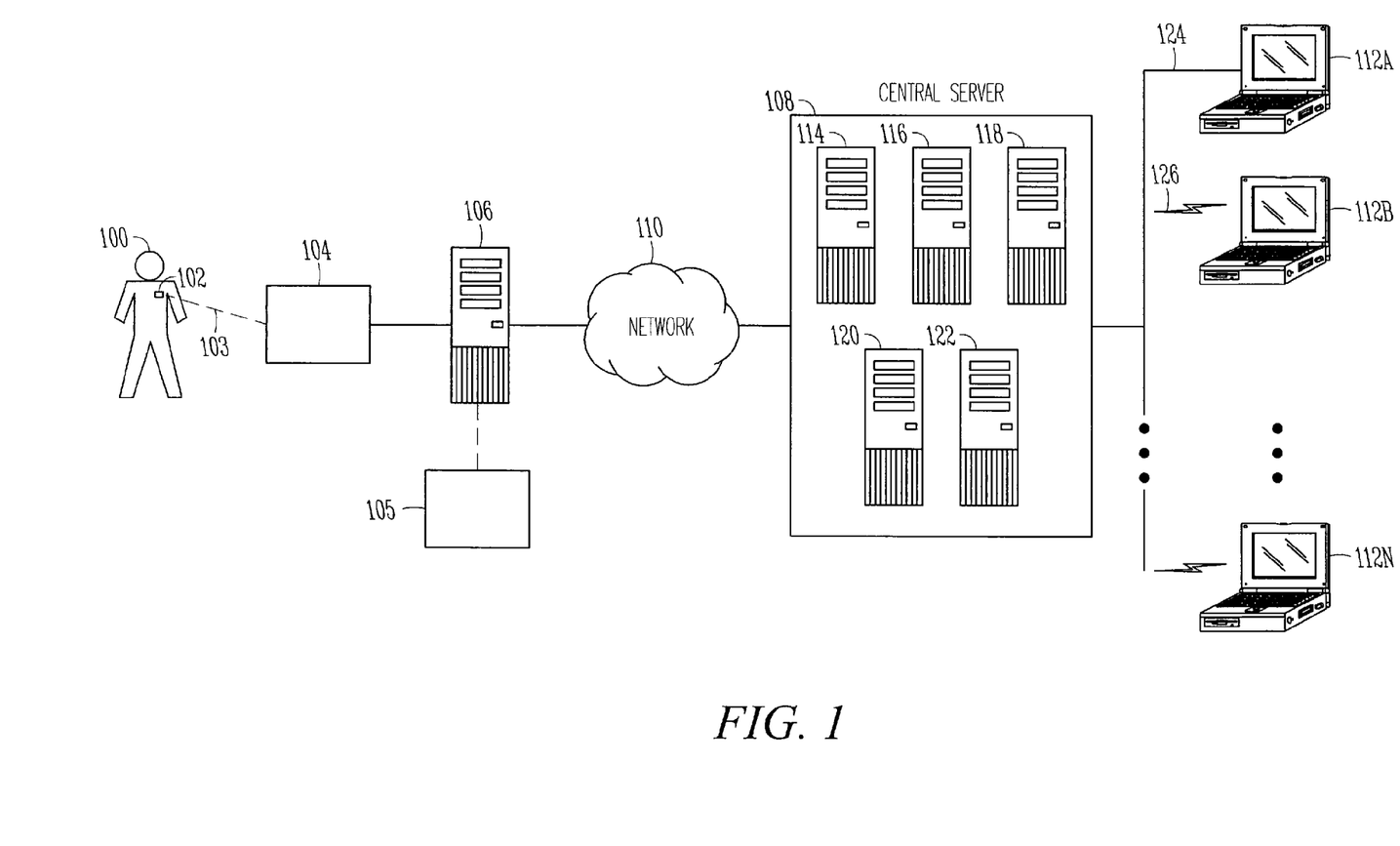
FIG. 1 is a schematic view illustrating portions of an example of a system that enables physician-patient communication.

FIG. 1 is a schematic view illustrating portions of an example of a system that enables physician-patient communication. In the example of FIG. 1, a patient 100 is provided with an IMD 102. Implanted medical devices may be configured to perform one or more operations, such as sensing one or more patient indications, recording any such indications, analyzing such indications, and providing one or more therapies based on the one or more such indications. In some examples, the IMD 102 is capable of sensing physiological data and storing such data for later communication.

Devices implanted within the body may have the ability to sense, communicate, or provide therapy. Implantable devices can provide direct measurement of characteristics of the body, including, without limitation, electrical cardiac activity (e.g., a pacemaker, cardiac resynchronization management device, defibrillator, etc.), physical activity, temperature, heart rate, blood pressure, breathing pattern, ejection fraction, blood viscosity, blood chemistry, blood glucose level, and other patient-specific clinical physiological parameters, while minimizing the need for patient compliance with such monitoring.

A heart rhythm sensor, typically found in a pacemaker or defibrillator, is one example of implantable device. In the heart, an electrical depolarization wave activates the heart muscle just prior to its contraction. Electrical circuits and lead-wires transduce the heart's activation event. By measuring the time interval between activation events, the heart rhythm can be determined.

A transthoracic impedance sensor is another example of an implantable device. In some examples, a transthoracic impedance sensor is included in a pacemaker, defibrillator, or other implantable medial device. Breathing passes large volumes of air into and out of the lungs. The electrical impedance of the thorax changes markedly because of large differences in conductivity of air and body tissues. The thoracic impedance can be measured during respiration and converted into a measurable electrical signal so that breathing rate and profile can be approximated.

Implantable devices can also sense one or more chemical conditions, such as glucose level, blood oxygen level, or the like. Other implantable devices, such as drug pumps, neurological devices (e.g., stimulators), oxygen sensors, or the like, may provide additional physiological measurements of the patient.

Derived measurements can also be determined from implantable devices. For example, a sleep sensor can rely on measurements taken by an implanted accelerometer that measures body activity levels. The sleep sensor can estimate sleeping patterns based on the measured activity levels. Other derived measurements can include a functional capacity indicator, autonomic tone indicator, sleep quality indicator, cough indicator, anxiety indicator, and cardiovascular wellness indicator quantifying a patient's overall health and well-being.

The IMD 102 communicates with an external transceiver 104, such as by using a wireless communication link 103. Typically, the IMD 102 receives commands from the transceiver 104. In some examples, the IMD 102 can transfer physiological or other patient information to the transceiver 104. In other examples, the IMD 102 communicates raw signal data to the transceiver 104, which may then communicate the signal data to another computer for processing. Typically, the transceiver 104 is located in close proximity to the patient 100. The transceiver 104 may be included within a personal computer or a specialized device, such as an IMD programmer or a personal digital assistant (PDA). In an example, the transceiver 104 is a hand-held device that is capable of connecting to a local computer 106. The connection can be made using a hard-wired connection (e.g., serial, USB, Firewire) or a wireless connection (e.g., RF, IR). In some examples, the local computer 106 is a specialized device (e.g., a home monitor station) or a personal computer.

One or more external devices 105 can be used to measure physiological data. Such devices 105 may include a multitude of devices to measure data relating to the human body, including temperature (e.g., a thermometer), blood pressure (e.g., a sphygmomanometer), blood characteristics (e.g., glucose level), body weight, physical strength, mental acuity, diet, heart characteristics, and relative geographic position (e.g., a Global Positioning System ("GPS")). An external device 105 can also include one or more environmental sensors. The devices 105 can be placed in a variety of geographic locations (in close proximity to patient or distributed throughout a population) and can record non-patient specific characteristics such as, for example, temperature, air quality, humidity, carbon monoxide level, oxygen level, barometric pressure, light intensity, and sound.

External devices 105 can also include devices that measure subjective data from the patient. Subjective data includes information related to a patient's feelings, perceptions, and/or opinions, as opposed to objective physiological data. For example, the "subjective" devices can measure patient responses to inquiries such as "How do you feel?" and "How is your pain?" and "Does this taste good?". The device can prompt the patient and record subjective data from the patient using visual and/or audible cues. For example, the patient can press coded response buttons or type an appropriate response on a keypad. Alternatively, subjective data may be collected by allowing the patient to speak into a microphone and using speech recognition software to process the subjective data.

In addition, patient responses obtained during cognitive tests administered to the patient using the external device 105 can be collected and analyzed. For example, questions or tasks can be presented to a patient on a touch-sensitive computer display. Test results can be used directly or indirectly to determine an indication of the patient's cognitive function. For example, if a patient is provided a question concerning a factual matter, such as "What is the capital of Texas?", both the patient's response and the time that the patient took to respond can be used as indications of the patient's cognitive health by direct and indirect measure, respectively. Also, the accuracy of the patient's response may be used as an indirect measurement of cognitive function.

In an embodiment, an indirect test may include an activity, which although not necessarily designed to test cognitive function, may be analyzed to determine indications that reflect cognitive ability. For example, a patient may be presented a routine questionnaire, such as "How do you feel today?", using a home patient device. The patient's response time may be used as an indirect metric indicating the patient's cognitive function. The patient's questionnaire may be provided using a touch-sensitive computer display, as described above, presenting a happy face, a neutral face, and a frowning face to use in response to the query. In such a configuration, other metrics may be obtained that could be used to derive a patient's cognitive function, such as the accuracy of where the patient touched the screen in relation to the graphical indicator, the pressure the patient used when activating the indicator, a number of attempts before a graphical indicator was activated or how long the patient touched the graphical indicator. Measurements such as these may indicate a loss of balance, hand-eye coordination or a reduction in mental acuity, each of which can be used as additional indicators of cognitive function.

The external device 105 can be utilized to provide one or more cognitive tests to the patient 100. Tests may include one or more questionnaires, such as a mini mental state examination (MMSE), an abbreviated mental state test, or other types of interrogatory testing. Tests may also include activities, such as clock drawing, digit spanning, digit symbol tasks or letter cancellation tests.

In various embodiments, patient indications, such as physiological data, are collected before, during, or after a cognitive function test is administered. In some examples, a patient's evoked response to a cognitive test may provide useful clinical information.

In an example, a patient's reaction time, accuracy, or other testing data, such as the date and time of the test, are communicated to the local computer 106, to be uploaded to the central server system 108. In some examples, the local computer 106 can perform analysis and deliver therapy or patient advice. In other examples, the local computer 106 acts as a conduit to the central server system 108, which performs data analysis and communicates results to the patient 100 via the local computer 106.

In certain examples, the local computer 106 is adapted to communicate with a central server system 108. The communication link between the local computer 106 and the central server system 108 is typically made through a wide-area network 110, such as the Internet. In some examples, the central server system 108 comprises one or more computers, such as a database server 114, a network server 116, a file server 118, an application server 120 or a web server 122. In certain examples, one or more terminals 112A, 112B, . . . , 112N are connected to the central server system 108. The terminals 112 are communicatively coupled to the central server system 108 using a wired 124 and/or a wireless connection 126. Typically, a user (e.g., the patient's attending clinician) may connect to the central server system 108 using a terminal 112, such as to query a patient's personal data or medical history, to initiate commands that administer therapy to the patient, program the transceiver 104, or to provide notes or comments that are recorded in the central server system 108 and optionally communicated to the patient 100.

Figure 2:
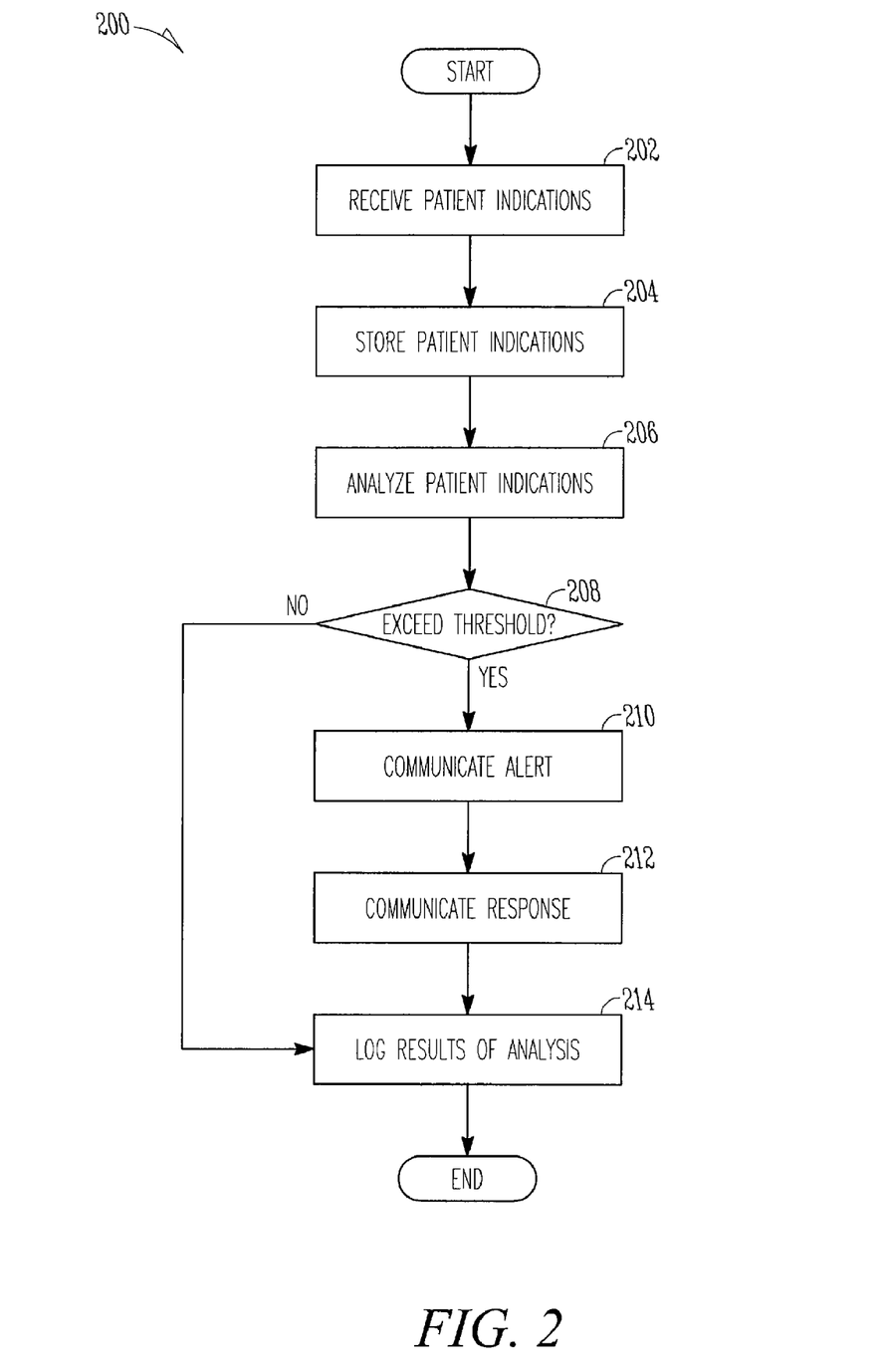
FIG. 2 is a flowchart illustrating generally a method for using patient data to determine a level of cognitive function.

FIG. 2 is a flowchart illustrating generally a method 200 for using patient data to determine a level of cognitive function. At 202, one or more patient indications are received. Patient indications can include physiological patient data or subjective patient data, such as patient interrogatory data. In some examples, the patient indications are supplied to a central server system 108, as illustrated in FIG. 1. The patient indications can, for example, be uploaded on a regular basis or when a patient connects to the central server system 108. Alternatively, in some examples, some or all of the patient's indications are provided directly to the central server system 108 without the use of a local repeater (e.g., local computer 106) using a wireless connection, such as a satellite link, cellular phone system, or microwave communication system. This may have the advantage of increasing patient compliance by removing manual patient operations. For example, an elderly or other patient with low capacity may be unable to unwilling to regularly use a local computer 106 to connect with the central server system 108 in order to upload patient data. In such cases, using a communication system that requires very little, or no, user interaction can increase the reliability of any diagnosis of co-morbidity conditions, such as cognitive function.

At 204, the patient indications are stored at the central server system 108. In one example, when patient indications are received they are stored in the database server 114. In other examples, patient indications are stored in a distributed database system.

At 206, the patient indications are analyzed. In some examples, one or more static values are used as threshold numbers to which the patient indications are compared. For example, in a test that requires a patient to touch four numbered corners of a computer display in ascending order, if the patient takes longer than ten seconds to do so, then the patient automatically fails that cognitive function test. In other examples, the patient's indications are recorded and used in the context of the patient's history of results, e.g., trended data. When using trended data, the relevant time interval may be adjusted by the clinician to view long-term and short-term trends in one or more cognitive function tests. In some examples, multiple time frames are used in a weighted manner, for example, decreases in function over a longer period of time may be considered less significant than decreases over a short period. In still other examples, the patient's results are compared to a population database. The use of a population database may increase the reliability of a diagnosis.

In some examples, one or more physiological indications are used either alone or in conjunction with cognitive test results to determine the likelihood of heart failure decompensation. For example, a poor result on one or more cognitive tests may indicate a co-morbidity of heart failure. The association between the poor results and a possible cognitive dysfunction due to heart failure can be verified by analyzing cerebral blood flow as detected, for example, by an implanted medical device. In another example, using a clinically-observed inverse relationship between hemodynamic pressure and cognitive function, a clinician could use IMD pressure data to reinforce the findings of a poor cognitive test performance. In a further example, a significant reduction of cardiac output may be related to cerebral underperfusion, which may explain cognitive dysfunction. In a further example, an implantable device can monitor patient fatigue, such as by trending thoracic fluid overload or sleep disordered breathing. Reduced activity, which may be caused by fatigue, may be both a symptom and a cause of depression and reduced cognitive function.

At 208, one or more threshold conditions are evaluated. For example, if trended data is analyzed in block 206, then a certain amount or percentage of decrease in the trended data for a particular patient indication can be used as a threshold condition.

At 210, if a threshold condition exists, then an alert may be generated to notify the patient or the attending clinician. Alerts can be as simple as a comment inserted into a patient's electronic chart or more complex, such as a page or phone call to the attending clinician on record. In an example, a supplementary alert is generated to notify the patient of the results of the analysis from block 206. In other examples, other alerts are generated depending on the type and severity of the patient's condition. For example, if the patient's indications represent an immediate threat to health, then a local medical response team or a member of the patient's family can be notified.

At 212, one or more responses are communicated to the patient or the patient's monitoring device (e.g., an IMD 102). In an example, a response is generated as a result of the existence of the threshold condition. Responses may be provided by the patient's physician or automatically, such as by the central server system 108. In various examples, the response includes at least one of adjusting one or more settings for an IMD 102, providing educational information to the patient, or scheduling an in-person visit, either at the patient's home or at the physician's office. In an example, adjusting the one or more settings of an IMD include adjusting setting for bradycardia therapy or adjusting settings for other cardiac resynchronization therapy.

At 214, the results of the analysis from block 206 are recorded. In an example, the recorded data includes the patient's identification information (e.g., name, chart number, social security number), a reference to the patient indications, a date and time of the analysis, a result of the analysis, an action taken as a result of the analysis, and clinician comments or feedback on the particular patient indications.

Figure 3:
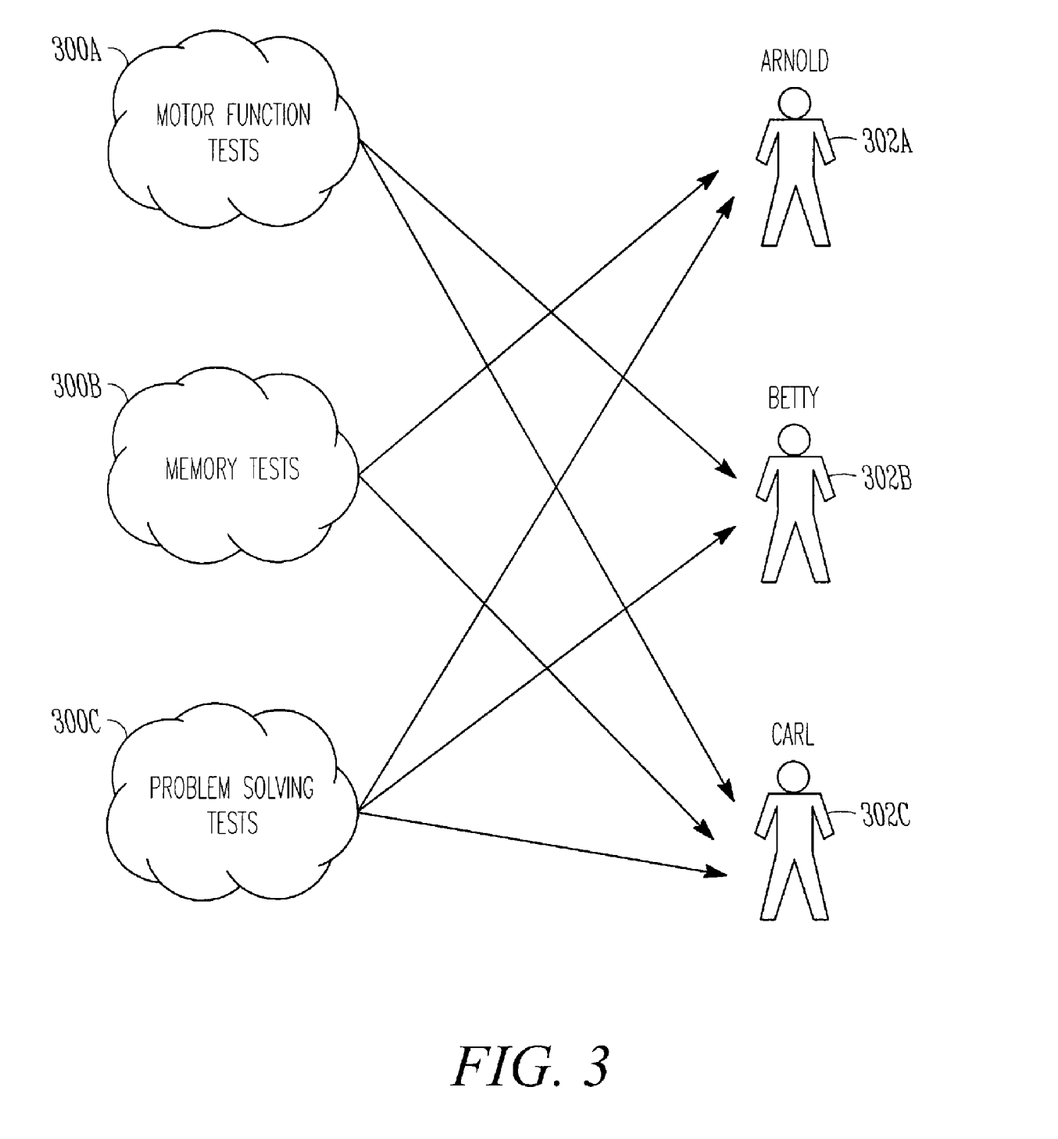
FIG. 3 is a diagram illustrating associations between patients and cognitive tests.

In some examples, cognitive tests are separated and identified by types. FIG. 3 illustrates three types of cognitive tests 300A, 300B, 300C and associations with three patients 302A, 302B, and 302C. In FIG. 3, the cognitive tests are separated into three groups: motor function 300A, memory 300B, and problem solving 300C. In certain examples, patients are provided different suites of tests depending on known pre-existing conditions. For example, if Arnold 302A is unable to move his fingers, such as is the case if Arnold is a paraplegic, then certain motor function tests may be inapplicable. Accordingly, Arnold 302A can be administered the memory 300B and problem solving 300C tests. Betty 302B however, while able to take advantage of all tests, may have a known pre-existing condition affecting her memory, such as Alzheimer's disease. In her case, Betty 302B is only associated and provided with the motor function 300A and problem solving 300C tests. The third patient, Carl 302C, has no known prior conditions that may affect testing and so he is associated with and provided all three types of tests, or a combined test that incorporates each test type.

In some examples, cognitive tests are grouped into tiers and patients are provided tests in a particular tier. In certain examples, upon failing a test in a particular tier, a patient is then administered a test from the next progressive tier. Certain tests may have the capability of providing better insight into a patient's heart failure condition. For example, in heart failure patients, memory and attention deficits are generally the most frequently occurring disorders, followed by psychomotor function and problem solving function. By testing memory in a first tier, and motor response times and problem solving only conditionally in successive tiers, the burden of test taking on the patient is reduced and patient compliance may be increased. In other examples, cognitive function tests are tiered such that one tier has generally more sensitive tests and another tier has generally more specific tests. In another example, cognitive function tests are tiered such that one tier has generally more precise tests and another tier has generally more accurate tests, where precision includes an ability of a measurement to be consistently reproduced and accuracy includes an ability of a measurement to match the actual value of the quantity being measured. Under certain conditions, patients may benefit by being administered additional cognitive function tests that hone in on a particular issue or reinforce an initial finding.

In an example, one or more reports can be generated using the stored cognitive function information. The reports can reflect such things as patient compliance, health and cognitive function trend data, specific health issues (e.g., an recorded arrhythmia or other physiological abnormality on a particular date, an anomalous result of a cognitive function test), and tests provided. Such data can be useful in diagnosing or providing feedback to the patient and as general population data for use with other patients with similar conditions.

Figure 4:
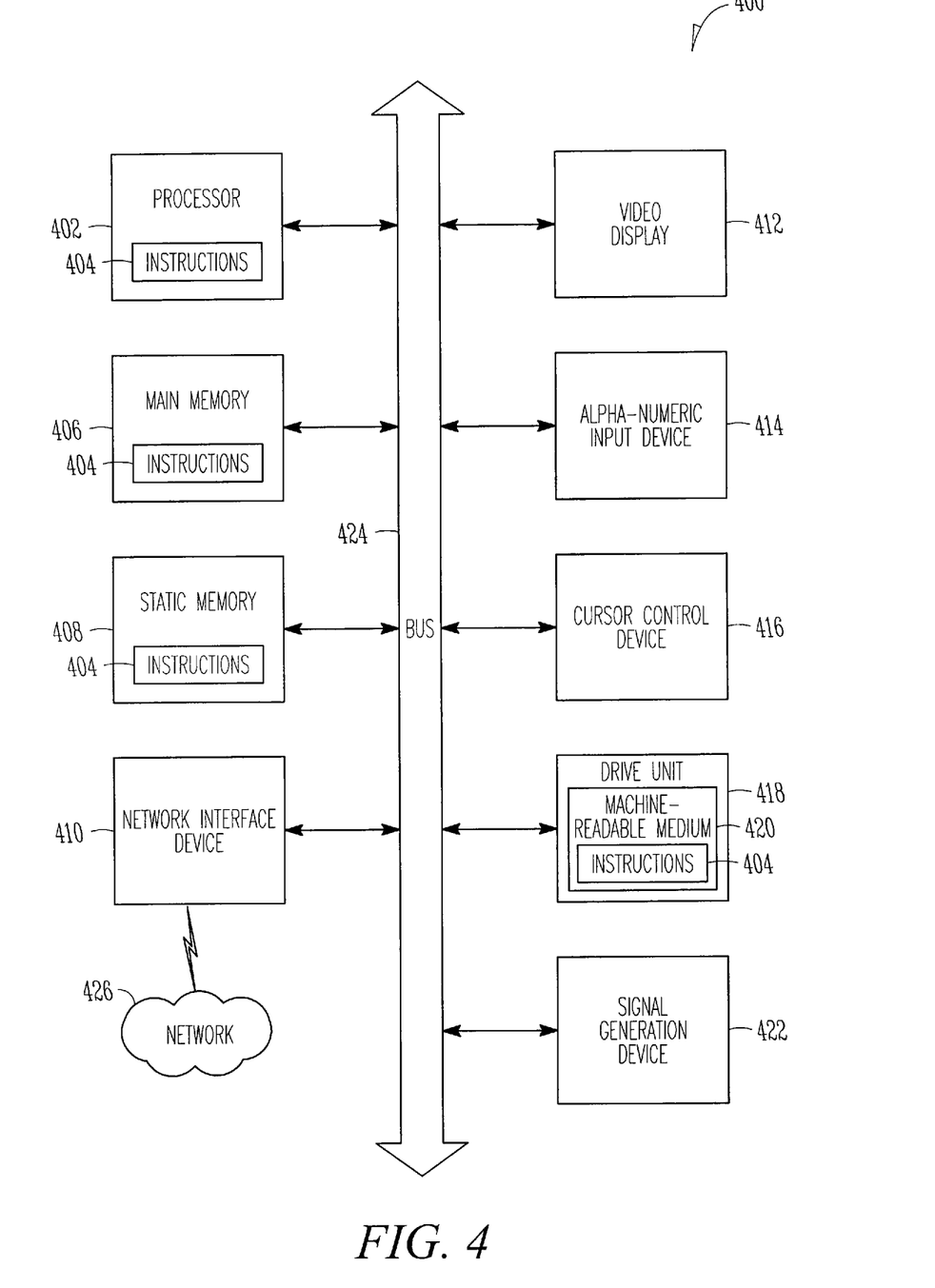
FIG. 4 illustrates a diagrammatic representation of a machine in the exemplary form of a computer system within which a set or sequence of instructions, for causing the machine to perform any one of the methodologies discussed herein, may be executed.

FIG. 4 illustrates a diagrammatic representation of a machine in the exemplary form of a computer system 400 within which a set or sequence of instructions, for causing the machine to perform any one of the methodologies discussed herein, may be executed. In alternative embodiments, the machine may comprise a computer, a network router, a network switch, a network bridge, Personal Digital Assistant (PDA), a cellular telephone, a web appliance, set-top box (STB) or any machine capable of executing a sequence of instructions that specify actions to be taken by that machine.

The computer system 400 includes a processor 402, a main memory 406 and a static memory 408, which communicate with each other via a bus 424. The computer system 400 may further include a video display unit 412 (e.g., a liquid crystal display (LCD) or a cathode ray tube (CRT)). The computer system 400 also includes an alphanumeric input device 414 (e.g., a keyboard), a cursor control device 416 (e.g., a mouse), a disk drive unit 418, a signal generation device 422 (e.g., a speaker) and a network interface device 410 to interface the computer system to a network 426.

The disk drive unit 418 includes a machine-readable medium 420 on which is stored a set of instructions or software 404 embodying any one, or all, of the methodologies described herein. The software 404 is also shown to reside, completely or at least partially, within the main memory 406 and/or within the processor 402. The software 404 may further be transmitted or received via the network interface device 410. For the purposes of this specification, the term "machine-readable medium" shall be taken to include any medium which is capable of storing or encoding a sequence of instructions for execution by the machine and that cause the machine to perform any one of the methodologies of the inventive subject matter. The term "machine-readable medium" shall accordingly be taken to include, but not be limited to, solid-state memories, optical and magnetic disks, and carrier wave signals. Further, while the software is shown in FIG. 4 to reside within a single device, it will be appreciated that the software could be distributed across multiple machines or storage media, which may include the machine-readable medium.

The foregoing description of specific embodiments reveals the general nature of the inventive subject matter sufficiently that others can, by applying current knowledge, readily modify and/or adapt it for various applications without departing from the generic concept. Therefore, such adaptations and modifications are within the meaning and range of equivalents of the disclosed embodiments. The phraseology or terminology employed herein is for the purpose of description and not of limitation. Accordingly, the inventive subject matter embraces all such alternatives, modifications, equivalents and variations as fall within the spirit and broad scope of the appended claims.

Method embodiments described herein may be computer-implemented. Some embodiments may include computer-readable media encoded with a computer program (e.g., software), which includes instructions operable to cause an electronic device to perform methods of various embodiments. A software implementation (or computer-implemented method) may include microcode, assembly language code, or a higher-level language code, which further may include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMS), read only memories (ROMs), and the like.

It is to be understood that the above description is intended to be illustrative and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72(b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A machine-assisted method comprising:
   receiving, at a processor-based system, a result of a cognitive test presented to a patient via a user interface, the cognitive test designed to measure cognitive ability by testing at least one of: motor function, memory, or problem solving ability of the patient; and
   using, at the processor-based system, the result of the cognitive test in determining a heart failure condition status of the patient.

2. The method of claim 1, further comprising:
   storing the result of the cognitive test;
   determining a testing trend over time, wherein the testing trend includes results of a series of instances of the cognitive test; and
   using the testing trend to determine a likelihood of heart failure decompensation.

3. The method of claim 1, further comprising:
   receiving a physiological indication related to the patient; and
   using the physiological indication in conjunction with the result of the cognitive test to determine a likelihood of worsening of the heart failure condition status.

4. The method of claim 3, wherein using the physiological indication in conjunction with the result of the cognitive test comprises:
   presenting an activity to the patient;
   detecting a changed physiological indication;
   correlating the changed physiological indication to the presented activity; and
   determining the likelihood of worsening of the heart failure condition status using the correlation between the changed physiological indication and the presented activity.

5. The method of claim 3, further comprising:
   storing the physiological indication;
   determining a physiological trend over time, wherein the physiological trend includes a series of instances of the physiological indication; and
   using the physiological trend to determine the likelihood of worsening of the heart failure condition status.

6. The method of claim 3, further comprising:
   storing the physiological indication;
   determining a physiological trend over time, wherein the physiological trend includes a series of instances of the physiological indication;
   storing the result of the cognitive test;
   determining a testing trend over time, wherein the testing trend includes a series of instances of the cognitive test; and
   using the physiological trend and the testing trend to determine the likelihood of worsening of the heart failure condition status.

7. The method of claim 3, wherein the physiological indication is obtained from an implanted medical device.

8. The method of claim 3, wherein the physiological indication includes a heart rate, a blood flow, a blood pressure, an impedance, or a heart vibration.

9. The method of claim 3, wherein the physiological data is received before, during, or after presenting the cognitive test to the patient.

10. The method of claim 1, wherein the cognitive test is a direct cognitive test.

11. The method of claim 10, wherein the direct cognitive test includes at least one of a questionnaire, a motor task, or a reaction task.

12. The method of claim 1, wherein the cognitive test is an indirect cognitive test.

13. The method of claim 12, wherein the indirect cognitive test includes one or more of a response time or an accuracy of response.

14. The method of claim 1, further comprising:
   providing to the patient a response that is initiated or adjusted using the likelihood of heart failure decompensation.

15. The method of claim 14, wherein the response includes at least one of titrating medication, adjusting one or more settings for an implanted patient device, providing educational information to the patient, or scheduling an in-person visit.

16. The method of claim 15, wherein adjusting the settings for the implanted patient device includes adjusting the settings for cardiac resynchronization therapy.

17. The method of claim 1, wherein using the results of the cognitive test comprises using a clinically-observed inverse relationship between hemodynamic pressure and cognitive function to determine the heart failure condition status.

18. The method of claim 1, comprising verifying the heart failure condition status by analyzing cerebral blood flow of the user.

19. A non-transitory machine-readable medium comprising instructions, which when executed by a machine, cause the machine to:
   receive a result of a cognitive test presented to a patient via a user interface, the cognitive test designed to measure cognitive ability by testing at least one of: motor function, memory, or problem solving ability of the patient; and
   use the result of the cognitive test in determining a heart failure condition status of the patient.

20. A system comprising:
   a processor; and
   a memory, the memory comprising instructions, which when executed by the processor, cause the processor to:
      receive a result of a cognitive test presented to a patient via a user interface, the cognitive test designed to measure cognitive ability by testing at least one of: motor function, memory, or problem solving ability of the patient; and
      use the result of the cognitive test in determining a heart failure condition status of the patient.

* * * * *